United States Patent [19]

Ratcliffe

[11] Patent Number: 5,089,294
[45] Date of Patent: Feb. 18, 1992

[54] PREPARATION OF CONDUCTIVE FILMS

[75] Inventor: Norman M. Ratcliffe, Bristol, England

[73] Assignee: British Aerospace plc, London, England

[21] Appl. No.: 557,749

[22] Filed: Jul. 26, 1990

[30] Foreign Application Priority Data

Aug. 4, 1989 [GB] United Kingdom ............... 8917937

[51] Int. Cl.⁵ ............................................ B05D 5/12
[52] U.S. Cl. .................................... 427/108; 427/58;
427/261; 427/374.1; 427/385.5; 427/389.7;
427/393.5; 427/407.2; 427/412.5; 427/430.1;
427/443.2
[58] Field of Search ................. 427/372.2, 374.4, 58,
427/108, 261, 374.1, 385.5, 389.7, 393.5, 407.2,
412.5, 430.1, 443.2

[56] References Cited

FOREIGN PATENT DOCUMENTS 0206414 6/1986 European Pat. Off. .
2169608A 12/1985 United Kingdom .

OTHER PUBLICATIONS

Patent Abstracts of Japan, vol. 10, No. 49 (P-461) (2206) 30 May 1986, & JP-A-61 003040 (Nitsushin Denki) 9 Jan. 1986.

*Primary Examiner*—Bernard Pianalto
*Attorney, Agent, or Firm*—Nixon & Vanderhye

[57] ABSTRACT

An electrically-conductive polypyrrole film is formed, on a non-conducting substrate, by contacting the substrate with pyrrole and an oxidising agent in a solvent, or with the colloidal polypyrrole that is the reaction product thereof, and removing the substrate while the film is at least substantially transparent, e.g. 50 to 250 nm thick. A gas sensor comprises a chemiresistor prepared by this process.

18 Claims, No Drawings

PREPARATION OF CONDUCTIVE FILMS

FIELD OF THE INVENTION

This invention relates to the preparation of conductive films and their use as gas sensors, in particular as sensor systems for the detection of atmospheric hydrazines and ammonia.

BACKGROUND OF THE INVENTION

Large quantities of hydrazines are used as fuels. The toxicity and possible carcinogenicity of the vapours require air monitoring for personnel safety.

Known hydrazine sensors are generally complex. For example, FR-A-2331791 discloses a gas detector apparently capable of detecting low levels of (dimethyl)hydrazine in air, comprising a combination of an ionisable detector and a gas scrubber.

U.S. Pat. No. 3549329 discloses a sensor for reducing vapours, including hydrazine and unsymmetrical dimethylhydrazine, comprising a noble metal thin film partially covered by a thin layer of a reducible metal salt; the salt lowers the electrical resistance of the film when exposed to the reducing vapour.

Polypyrrole-coated chemiresistors, sensitive to ammonia, are known.

Miasik et al, Conducting Polymers, Alcacer (ed.), D.Reidel Publishing Company (1987) 189-197, disclose forming thin polypyrrole films by electropolymerisation from aqueous solutions of the monomer and $LiBF_4$. The film was sensitive to 0.1% ammonia in air, and also sensitive to other gases.

Ojio et al, Polymer Journal 18(1) (1986) 95-98, disclose transparent, conducting polypyrrole-polyvinyl alcohol composite films formed by exposing PVA films containing ferric chloride to pyrrole vapour. The properties of the polypyrrole film are apparently similar to those of polypyrrole prepared by electrochemical polymerisation.

Armes et al, J. Chem. Soc., Chem. Commun. (1987) 288-290, disclose the preparation of conducting polypyrrole particles by dispersion polymerisation in aqueous medium, using ferric chloride as the initiator. A concentrated system was used, and stirring was maintained for at least 16 hours.

SUMMARY OF THE INVENTION

The present invention is based on the discovery that chemiresistors including a highly sensitive polypyrrole film can be prepared by the simple procedure of dipping a non-conducting substrate in, or otherwise contacting the substrate with, a colloidal suspension of polypyrrole (which is prepared from an oxidising agent and pyrrole). The coated substrate conducts electricity, and the resistance changes reversibly in the presence of hydrazine and ammonia.

DESCRIPTION OF THE INVENTION

A chemiresistor sensitive to ammonia and hydrazine can be obtained by contacting a non-conducting substrate with polypyrrole in water, in the presence of an oxidising agent, and drying the coated substrate.

More specifically, an ammonia/hydrazine-sensitive chemiresistor may be produced by adding pyrrole, or an aqueous solution of pyrrole, with stirring, to an aqueous solution of an oxidising agent, e.g. ferric ions. A non-conducting substrate is then coated by being placed in the solution. After a period which may be less than 3 hours, e.g. about 30 minutes, the coated substrate is removed, washed with water and dried, e.g. at ambient temperature. Contacts can be provided on the polypyrrole coating by any of various methods, e.g. by the application of conducting paint.

The morphology of polypyrrole particles which are formed by the process of the invention has been described by Armes et al (see above). However, according to the present invention, coatings of particles onto substrates are described; the substrate is coated for a relatively short time, not only because it is economical, but also because, while relatively thick coatings can be formed, after a longer coating time, they tend to have reduced conductivity and also reduced bonding to the substrate, i.e. they can fall off. Low concentrations of pyrrole can be used.

In general terms, the process of the invention is conducted to a point at which the polypyrrole film is substantially transparent, e.g. to a thickness of 40 to 300, preferably 70 to 200 nm, e.g. about 50 nm (500 Angstrom units). The substrate may be opaque or transparent, and in the latter case the product of the process is itself transparent. The product can then by used as, for example, a conducting window.

With respect to a transparent substrate, the transmission of the product is preferably reduced by not more than 50%, more preferably less than 20 or 30%, at a given wavelength. For example, the transmission is 96.5% at a film thickness of about 50 nm (by electron microscopy), and 20.6% at about 235 nm, according to the Beer-Lambert law. Transmission is generally independent of wavelength (in the visible spectrum); 700 nm is a suitable standard.

By way of example, the substrate may be glass or acrylic or polyester, e.g. ICI-Melanex or polymethyl methacrylate. A substrate having a degree of thermoplasticity, such as Perspex, is preferred, since the bonding of the polypyrrole film to the substrate can then be enhanced by heating the substrate to a temperature at which it softens, followed by cooling. It appears that the polypyrrole particles may engage more closely with the substrate at or around its softening point, e.g. by diffusion bonding.. For use as a chemiresistor, the product may be in the form of, for example, rods or plates.

The following Example illustrates the invention.

EXAMPLE

Pyrrole (370 mg.) was dissolved in water (15 $cm^3$) and added to freshly-prepared ferric nitrate solution (27 g in 800 $cm^3$), with stirring. Strips of clean acrylic were then immersed in the solution, orthogonal to the water surface, and stirring ceased. The acrylic strips were removed at certain time intervals, washed thoroughly with distilled water (to remove loosely-adhering particles), and allowed to dry at room temperature for circa 3 hours. For sensor use, one coating was removed by rubbing with coarse tissue. The strips were then heated in vacuo at circa 140° C. for 1 hour (to diffusion-bond the polypyrrole spheres into the acrylic, its softening temperature) and removed from the vacuum at room temperature.

Sensors were then prepared: the heat-processed polypyrrole-coated acrylic was cut into 1 $cm^2$ squares and glued onto thin strips of vero board. The glue (electrolube) had a resistance >20 Mohms. Silver dag was used to make contact with the faces of the polypyrrole. The amyl acetate from the silver dag was either evaporated in vacuo at 80° C., for 1 hour, or the sensor was left for 24 hours in air.

The sensors were then tested: ammonia was injected, by means of a syringe, into a 2 litre flask with a tap and one neck containing a rubber septum. After circa 2 minutes, the sensor was rapidly placed into the flask and the rubber septum rapidly replaced. The resistance was measured by wires exiting through the rubber septum. After each test, the ammonia was expelled by evacuation and extensive flushing of the flask with air. The very lowest concentration of gas was measured, first to ensure there was no possibility of interference by ammonia adsorbed on the glass.

Hydrazine measurements were conducted similarly: a circa 1% vapour of hydrazine in air was prepared by passing 200 cm$^3$/min air through hydrazine hydrate and this was further diluted or the appropriate volume of 1% vapour injected into the 2 litre flask.

The spheres of polypyrrole are in contact, and the resistivity depended on the time immersed in the ferric ions. The longer the acrylic was left in the pyrrole-ferric ion solution, the thicker the film appeared to be, i.e. more opaque; however the resistance decreased with immersion time and then appeared to increase, although there was clearly denser coating. This is shown in Table 1, by the resistance readings taken 12 days after preparation. Table 1 also shows the transparency of films (1), (2), (3) and (4), for a film coating on both faces of the acrylic (1cm$^2$)

TABLE 1

| Film | Deposition Time(min) | Resistance (Mohm) | Transmission (729 nm, %) |
|---|---|---|---|
| Control acrylic | 0 | — | 91.1 |
| 1 | 30 | 2.22 | 45.7 |
| 2 | 50 | 1.25 | 29.0 |
| 3 | 170 | 0.53 | 10.3 |
| 4 | 220 | 2.79 | 10.7 |

For film (2) (both faces coated) and the uncoated acrylic, the following transmissions were observed:

TABLE 2

| Wavelength (nm) | 800 | 650 | 550 | 450 | 400 | 350 |
|---|---|---|---|---|---|---|
| Transmission (%): | | | | | | |
| acrylic | 86.1 | 91.1 | 88.9 | 87.9 | 87.7 | 27.9 |
| film (2) | 26.1 | 32.0 | 31.4 | 27.4 | 27.3 | 8.4 |

A clear Ohm's law relationship was observed up to the 350V tested. The temperature resistance relationship was reversible. The departure from linearity may be due to expansion effects due to the acrylic or polypyrrole spheres. The apparent anomaly of thicker films showing reduced conductivity, i.e. prepared by longer exposure times in the reaction vessel, may be due to acid degradation of the polypyrrole or to progressively coating with more and more acid-polymerised pyrrole, which is non-conducting. (It is well known that solutions of ferric salts become progressively acidic due to hydrolysis; furthermore the pyrrole releases H$^+$ on oxidative polymerisation.) An activation energy of 0.22 eV can be found from the gradient of the ln plot of resistivity with inverse of temperature.

Atmospheric effects on the polypyrrole coatings show some linear resistance relationship. It was shown that water reversibly physisorbed onto the polypyrrole coating was a significant factor responsible for these resistance changes, as 48 hours in a desiccator over anhydrous calcium chloride caused a significant resistance drop. Storage of the polypyrrole-coated acrylic in dry nitrogen also stopped the resistance increase with time.

The films were exposed to ca. 1% hydrazine for three minutes. An increase in resistance was observed. The resistances continue to rise if exposed beyond three minutes. There is an apparent relationship between thickness of polypyrrole and response to hydrazine, with a decrease in response with increase in thickness. With ceasure of exposure to hydrazine and exposure to air, the resistance initially quickly drops and then slowly drops towards its former value. Film (3) gives a low response, and the final resistance after ceasing exposure to hydrazine is less than the initial value. A speculative explanation for the latter phenomenon is that the hydrazine is displacing or interacting with adsorbed water on the polymer.

Films (1) and (2) were left exposed to air for 8 weeks to test their environmental stability, and then re exposed to ca. 1% hydrazine. Film (1) still showed a high response of 140K change in minutes, 36% of the former response, while film (2) showed an unexplained resistance decrease of 410K. When the sensors were exposed to air, after exposure to hydrazine, the resistance of film (1) quickly decreased as expected, while the resistance of film (2) remained virtually unchanged. Film (1) was subjected to several exposures of hydrazine and gave a similar reversible resistance increase, although the baseline resistance continued to increase. Several preparations of 12 week old film (1) with resistances of circa 3.5 Mohm gave reversible resistance increases of 0.16–0.30 Mohm with 100 ppm hydrazine and reversible increases of 0.03–0.08 Mohm with 25 ppm hydrazine.

There is a sharp increase in resistance when film (1) is exposed to 1%, 0.1%, 0.01%, 0.001%, 0.0001% and 0.00001% (100 ppb) ammonia, with a rapid return to circa the pre-exposure resistance when the film is placed in ammonia-free air. Even at 100 ppb, the resistance change was much greater than would arise due to water vapour and temperature changes. The initial resistance of film (1) was 2.3 Mohm. The film retains high sensitivity with time. The following results are for a film three months after preparation (measurements taken when max. reading reached, typically 1 minute, but * indicates measurements taken after 15 sec).

TABLE 3

| Ammonia (%) | 1.0* | 0.1* | 0.01 | 0.001 | 0.0001 | 0.00001 |
|---|---|---|---|---|---|---|
| Resistance change (Mohms) | 1.4 | .24 | 1.02 | 0.47 | 0.25 | 0.16 |

What I claim is:

1. A process for preparing an electrically-conductive polypyrrole film on an electrically non-conducting substrate, which comprises the steps of:
    contacting the substrate with pyrrole and an oxidising agent in a solvent thereby forming a film on said substrate, and
    removing the substrate and film from said contact while the film is at least substantially transparent.

2. A process according to claim 1, wherein the substrate is transparent.

3. A process according to claim 1, wherein the film is 50 to 250 nm thick.

4. A process according to claim 1, wherein the film has a transmission value of at least 70%.

5. A process according to claim 1, wherein the substrate is thermoplastic.

6. A process according to claim 5, which comprises the additional steps of subjecting the polypyrrole-coated substrate to heating, to about the softening point of the substrate, and cooling.

7. A process according to claim 1, further including the additional step of providing an electrical contact on the polypyrrole film.

8. A process according to claim 7, wherein said providing step includes the application of a conductive paint.

9. A process according to claim 1, wherein the film is 40 to 300 nm thick.

10. A process for preparing an electrically-conductive polypyrrole film on an electrically non-conductive substrate, which comprises the steps of:
    contacting the substrate with a colloidal polypyrrole comprising a reaction product of pyrrole and an oxidising agent, thereby forming a film on said substrate; and
    removing the substrate and film from said contact while the film is at least substantially transparent.

11. A process according to claim 10, wherein the substrate is transparent.

12. A process according to claim 10, wherein the film is 50 to 250 nm thick.

13. A process according to claim 10, wherein the film has a transmission value of at least 70%.

14. A process according to claim 10, wherein the substrate is thermoplastic.

15. A process according to claim 14, which comprises the additional steps of subjecting the polypyrrole-coated substrate to heating, to about the softening point of the substrate, and cooling.

16. A process according to claim 10, further including the additional step of providing an electrical contact on the polypyrrole film.

17. A process according to claim 16, wherein said providing step includes the application of a conductive paint.

18. A process according to claim 10, wherein the film is 40 to 300 nm thick.

* * * * *